(12) United States Patent
Steiner, III (10) Patent No.: US 9,700,695 B2
(45) Date of Patent: Jul. 11, 2017

(54) ANTI-ASPIRATION MASK SYSTEM

(71) Applicant: James E Steiner, III, Las Vegas, NV (US)

(72) Inventor: James E Steiner, III, Las Vegas, NV (US)

(*) Notice: Subject to any disclaimer, the term of this patent is extended or adjusted under 35 U.S.C. 154(b) by 424 days.

(21) Appl. No.: 14/562,705

(22) Filed: Dec. 6, 2014

(65) Prior Publication Data
US 2015/0157817 A1    Jun. 11, 2015

Related U.S. Application Data

(60) Provisional application No. 61/913,056, filed on Dec. 6, 2013.

(51) Int. Cl.
| | |
|---|---|
| *A61M 16/06* | (2006.01) |
| *A61M 16/20* | (2006.01) |
| *A61M 16/08* | (2006.01) |
| *A61M 1/00* | (2006.01) |

(52) U.S. Cl.
CPC .......... *A61M 16/06* (2013.01); *A61M 1/0023* (2013.01); *A61M 16/0683* (2013.01); *A61M 16/0816* (2013.01); *A61M 16/208* (2013.01); *A61M 2205/18* (2013.01); *A61M 2205/3306* (2013.01); *A61M 2205/3324* (2013.01); *A61M 2205/3334* (2013.01); *A61M 2205/3344* (2013.01); *A61M 2205/3375* (2013.01); *A61M 2205/3592* (2013.01)

(58) Field of Classification Search
None
See application file for complete search history.

(56) References Cited

U.S. PATENT DOCUMENTS

| | | | |
|---|---|---|---|
| 4,537,189 | A | 8/1985 | Vicenzi |
| 6,063,051 | A | 5/2000 | Stern |
| 6,971,389 | B2 | 12/2005 | Collins |
| 7,101,341 | B2 | 9/2006 | Tsukashima et al. |
| 7,297,120 | B2 | 11/2007 | Tsukashima et al. |
| 7,762,953 | B2 | 7/2010 | Derchak et al. |

(Continued)

OTHER PUBLICATIONS

Engelhardt, T., and N. R. Webster. "Pulmonary Aspiration of Gastric Contents in Anaesthesia." British Journal of Anaesthesie 83.3 (1999): 453-60.].

*Primary Examiner* — Rachel Young
(74) *Attorney, Agent, or Firm* — Connie R. Masters (57) ABSTRACT

A medical mask system is provided that detects aspiration and/or vomit or misdirected oropharyngeal secretions, alerts medical staff, and removes any effluent to prevent pulmonary aspiration. The mask system includes a mask body for covering the wearer's mouth that is integrated with at least one aspiration-detecting sensor. The aspiration-detecting sensor is configured for detecting aspiration or effluent and is configured to provide an aspiration-detected signal. The signal is received by both an alerting device and a suction assembly that is actuated to provide suction to tubing attached to the mask body to remove any effluent from the mask body. The aspiration-detecting sensor may include, for example, one or more of a pH sensor, a pressure sensor, an oxygen flow sensor, an acoustic sensor, or an object recognition sensor. The alert, for example, may be provided to a nurse's station, at a patient's room, or to a mobile application.

19 Claims, 6 Drawing Sheets

(56) References Cited

U.S. PATENT DOCUMENTS

| | | |
|---|---|---|
| 2005/0217678 A1 | 10/2005 | McCormick et al. |
| 2006/0079942 A1 | 4/2006 | Deno et al. |
| 2012/0241084 A1 | 9/2012 | Nasir |
| 2012/0285455 A1 | 11/2012 | Varga et al. |
| 2012/0330111 A1* | 12/2012 | Borody ............. A61M 16/0488 600/301 |
| 2014/0150791 A1* | 6/2014 | Birnkrant .......... A61M 16/0006 128/204.23 |

* cited by examiner

ANTI-ASPIRATION MASK SYSTEM

CROSS-REFERENCE TO RELATED APPLICATIONS

This nonprovisional application claims the benefit of U.S. Provisional Patent Application Ser. No. 61/913,056, filed on Dec. 6, 2013, which is incorporated herein in its entirety.

FIELD OF INVENTION

This invention relates generally to medical devices, and, more particularly to a medical face mask with aspiration detection means, suction means and alerting means.

BACKGROUND OF THE INVENTION

Pulmonary aspiration is a serious medical problem. Pulmonary aspiration is defined as misdirection of oropharyngeal secretions or gastric contents into the larynx and/or the lower respiratory tract. Pulmonary aspiration may be the cause of various syndromes, but the most important include aspiration pneumonitis (caused by aspiration of gastric content) and aspiration pneumonia (caused by aspiration of oropharyngeal secretions colonized by bacteria). [Marik, Paul Ellis. Handbook of Evidence based Critical Care. New York: Springer, 2010; Marik, Paul E. "Pulmonary Aspiration Syndrome." Current Opinion in Pulmonary Medicine 17 (2011): 148-54.]

Pulmonary aspiration of gastric contents is a recognized and feared complication of general anesthesia. Pulmonary aspiration also frequently occurs in trauma or ICU patients with altered states of consciousness, such as head trauma, alcohol or drug-induced states and cerebrovascular accidents. [Crit Care Med. 2011 April; 39(4): 818-826.] If a patient is sedated, unconscious or otherwise disabled, gastric contents are more likely to be aspirated. Aspiration may result from obstruction of the pharynx, weakness or incoordination of the pharyngeal muscles, poor opening of the upper esophageal sphincter, or other impairments. [Mizuko, Mark. "Aspiration." Aspiration. University of Minnesota Duluth, Web. 10 Jul. 2013.] Administration of sedation can produce an unconscious patient at risk for developing emesis with pulmonary aspiration. During conscious sedation, procedural physicians may attempt to avoid this problem by administering sedatives sparingly, which, though reducing the risk of the complication, may also increase the chance that the patient does not receive adequate relief from pain outside the practice of anesthesiology. [http://www.ncbi.nlm.nih.gov/pubmed/1501047; http://felipeairway.sites.medinfo.ufl.edu/files/2009/11/sga-and-aspiration.pdf]

A relatively small amount of aspirate can cause significant problems or even death. The critical volume of aspirate sufficient to cause aspiration pneumonitis is often stated as 25 ml with a pH<2.5; this is derived from unpublished work on Rhesus monkeys, extrapolated to humans. [Engelhardt, T. and N. R. Webster. "Pulmonary Aspiration of Gastric Contents in Anaesthesia." British journal of Anaesthesie 83.3 (1999): 453-60.]

Each year many deaths occur in hospitals and nursing homes due to pulmonary aspiration. This is due both to the inability of patients to call for help (due to unrelated medical issues, coma, dementia, etc.) upon an aspiration event and the failure of nursing staff, using current monitoring practices, to detect many instances of pulmonary aspiration within a sufficient amount of time.

Currently, initial recognition of aspiration is possible by way of visible gastric contents in the oropharynx, or more subtle indications such as hypoxia, increased inspiratory pressure, cyanosis, tachycardia or abnormal auscultation. [King, Wendy. "Pulmonary Aspiration of Gastric Contents." Update in Anaesthesia 3 (2011): 28-31.] Long term symptoms of aspiration are bluish discoloration of the skin caused by lack of oxygen, chest pain, coughing up foul-smelling, greenish or dark phlegm (sputum) or phlegm that has pus or blood, fatigue, fever, shortness of breath, wheezing, breath odor, excessive sweating and/or problems swallowing. ["Health Guide." Aspiration Pneumonia. The New York Times Company, 24 Jan. 2013. Web. 10 Jul. 2013.]

A few patents have addressed emesis events. An aviator's breathing mask device that gives complete protection from external atmosphere while providing for disposal of effluent into an effluent receiver has been provided by Vicenzi in U.S. Pat. No. 4,537,189, which includes a one way valve leading to an expandable flexible bag for containing effluents. A face mask for police detainees with a central folded region open at the lower edge to receive effluents to prevent pooling of vomit within the mask is provided by Collins in U.S. Pat. No. 6,971,389. But none of these patents provide a system that will detect and notify medical personnel of an episode of aspiration.

Accordingly, there is a need for a system to assist in removing aspirate and to rapidly detect emesis and/or aspiration to allow a rapid response to the situation by attending medical staff.

BRIEF SUMMARY OF THE INVENTION

The present invention is directed to a medical anti-aspiration mask system that detects aspirate, alerts medical personnel and removes the aspirate from within the mask body, thereby reducing the risk of serious complications for the patient. The mask system includes a mask body for covering the wearer's mouth that is integrated with a suction system, an aspiration-detecting sensor system and an alerting system. The aspiration-detecting sensor is configured for detecting vomit, regurgitation, oropharyngeal secretions and/or aspiration and is configured to provide an aspiration-detected signal. The signal is received by both an alerting device and a suction assembly.

The several types of aspiration-detecting sensors are provided, which may be used alone or in combination. The aspiration-detecting sensor may include, for example, one or more of a pH sensor, an oxygen flow sensor, a pressure sensor, an acoustic sensor, or an object recognition system.

The alerting device provides an alert that notifies medical personnel of the emergency situation. The alert may be provided, for example, to a remote nurse's station, to an attendant in the patient's room, or to a mobile application.

The suction assembly provides suction to tubing attached to the mask body to suction any foreign material from the mask body.

An object of the present invention is to provide a medical mask system with a sensor to detect aspiration and/or effluent within the mask body which is positioned over the patient's mouth.

An additional object of the present invention is to provide a medical mask system that provides at least one alert to notify medical personnel of the aspiration event.

A further object of the present invention is to provide a medical mask system that delivers suction to the mask body upon detection of the aspiration event.

These and other objects, features and advantages of the present invention will become more readily apparent from the attached drawings and from the detailed description of the preferred embodiments which follow.

BRIEF DESCRIPTION OF THE SEVERAL VIEWS OF THE DRAWINGS

The preferred embodiments of the invention will hereinafter be described in conjunction with the appended drawings, provided to illustrate and not to limit the invention, where like designations denote like elements.

Like reference numerals refer to like parts throughout the several views of the drawings.

DETAILED DESCRIPTION OF THE INVENTION

Shown throughout the figures, the present invention is directed toward an anti-aspiration medical mask system, shown generally as reference number 10, that detects an aspiration event and/or detects vomit or oropharyngeal secretions within the mouth, and, upon detection of the event or the effluent, provides suction and provides an alert to medical personnel.

Since consequences of aspiration are highly dependent upon the condition of the patient, two embodiments are presented to accommodate these different situations. The mask system 10 of the first embodiment is designed for use with a patient 70 who is not sedated or who is lightly sedated and has full muscle control of their pharyngeal muscles. In case of aspiration, the individual is expected to have a gag reflex and be able to cough. As a result, when gastric content or oropharyngeal secretions are misdirected into the larynx the effluent will exit the mouth into the mask body 25. The mask system 10 of the second embodiment is designed for a comatose or fully sedated individual that has no muscle control of the pharyngeal muscles. In case of aspiration, the individual is not expected to cough or have a gag reflex. The effluent substances will most likely flow into the laryngeal inlet and follow down the trachea if the anti-aspiration medical mask system of the present invention is not in use.

Figure 1:
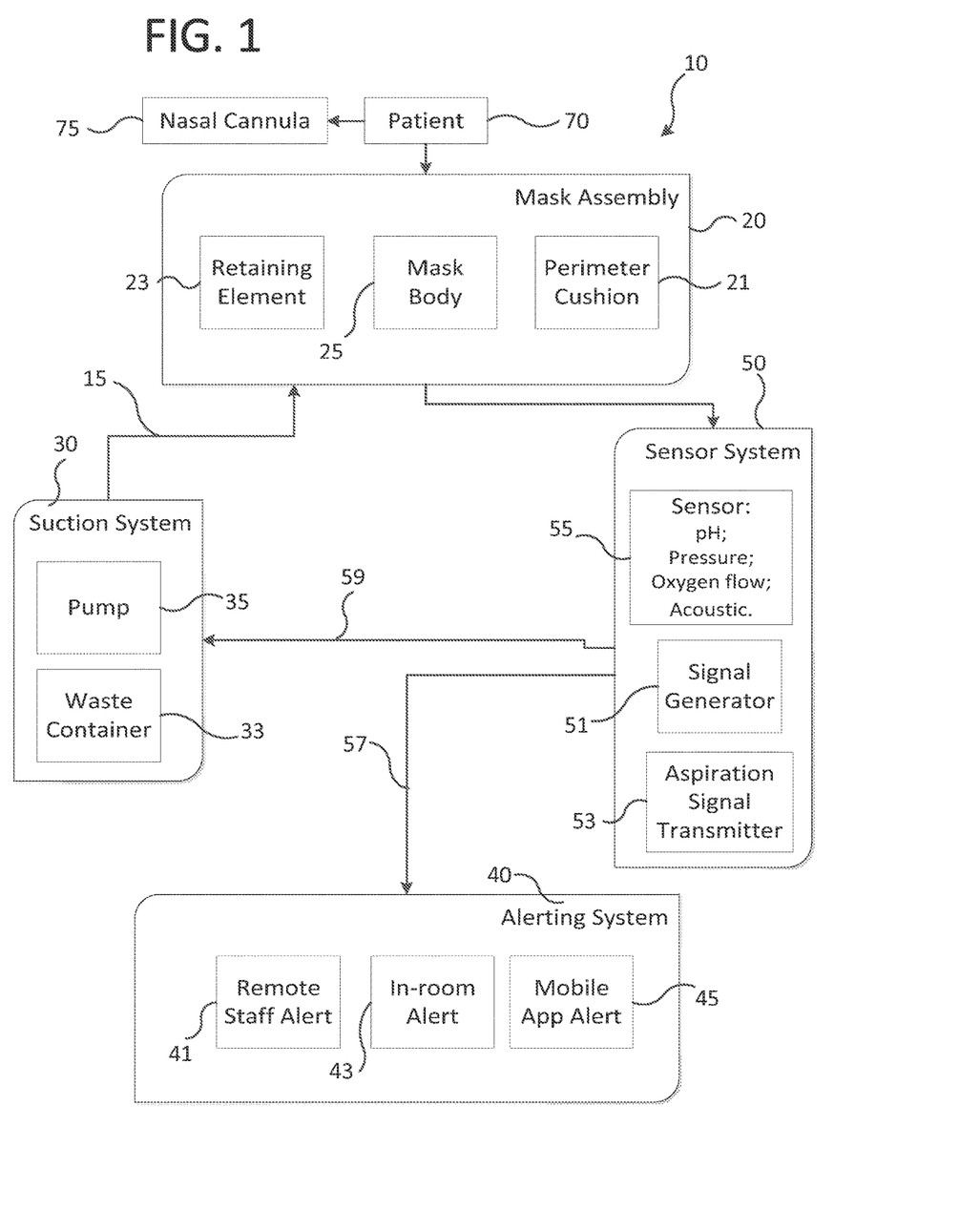
FIG. 1 is a diagram of a first aspect of the first embodiment of the anti-aspiration medical mask system of the present invention.
Figure 2:
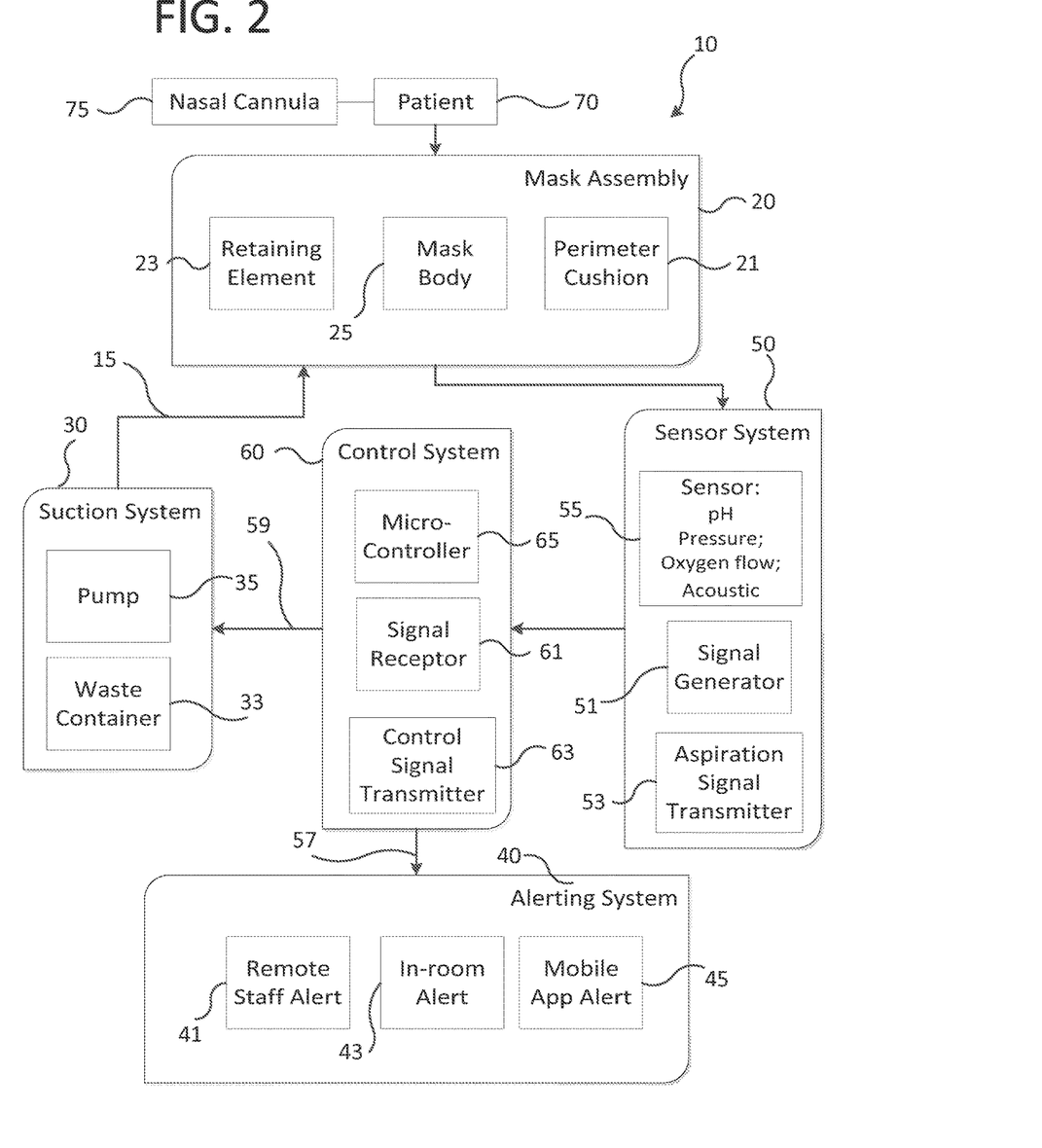
FIG. 2 is a diagram of a second aspect of the first embodiment of the anti-aspiration medical mask system of the present invention, which includes a control system.
Figure 7:
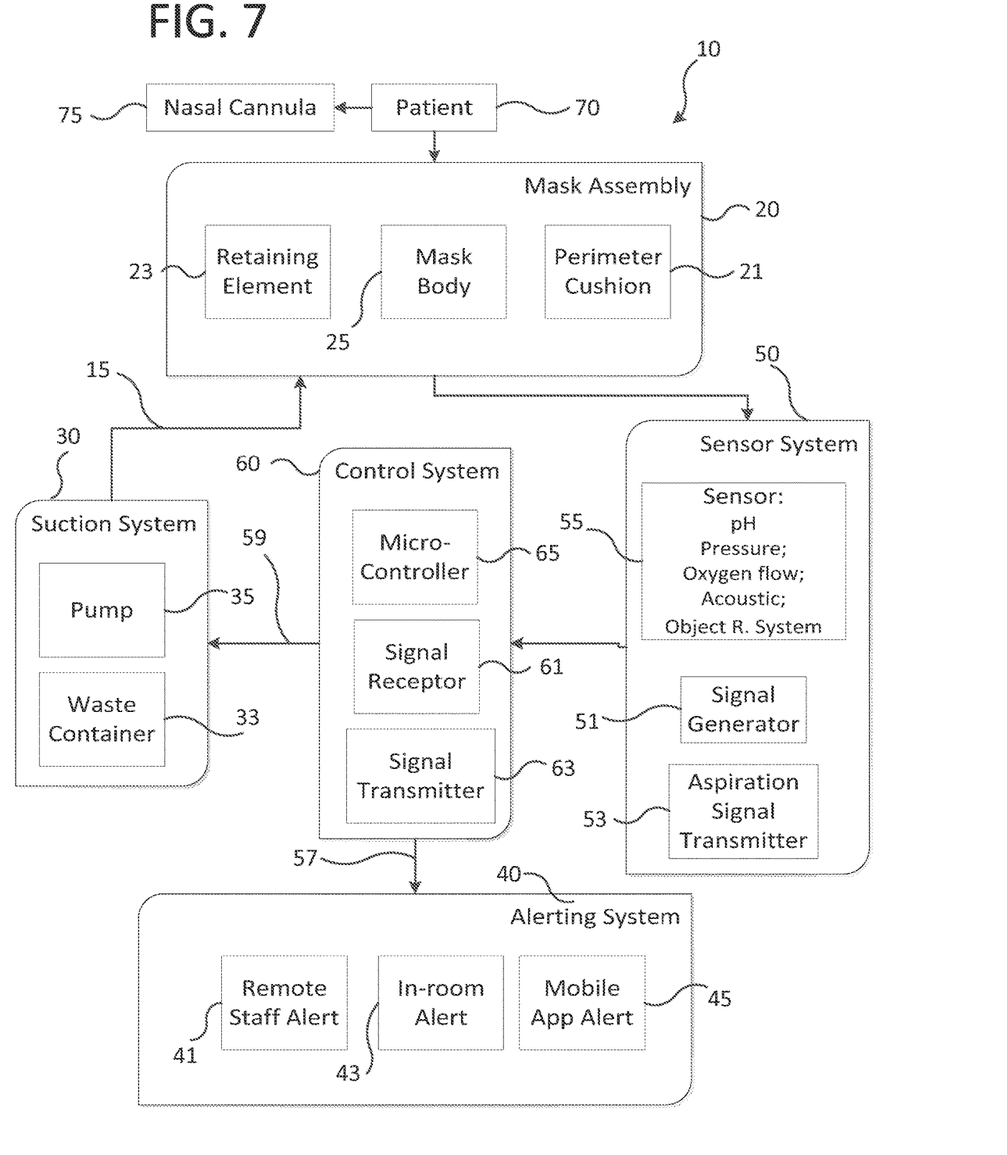
FIG. 7 is a diagram of a second aspect of the second embodiment of the anti-aspiration medical mask system of the present invention, which includes a control system.
Figure 8:
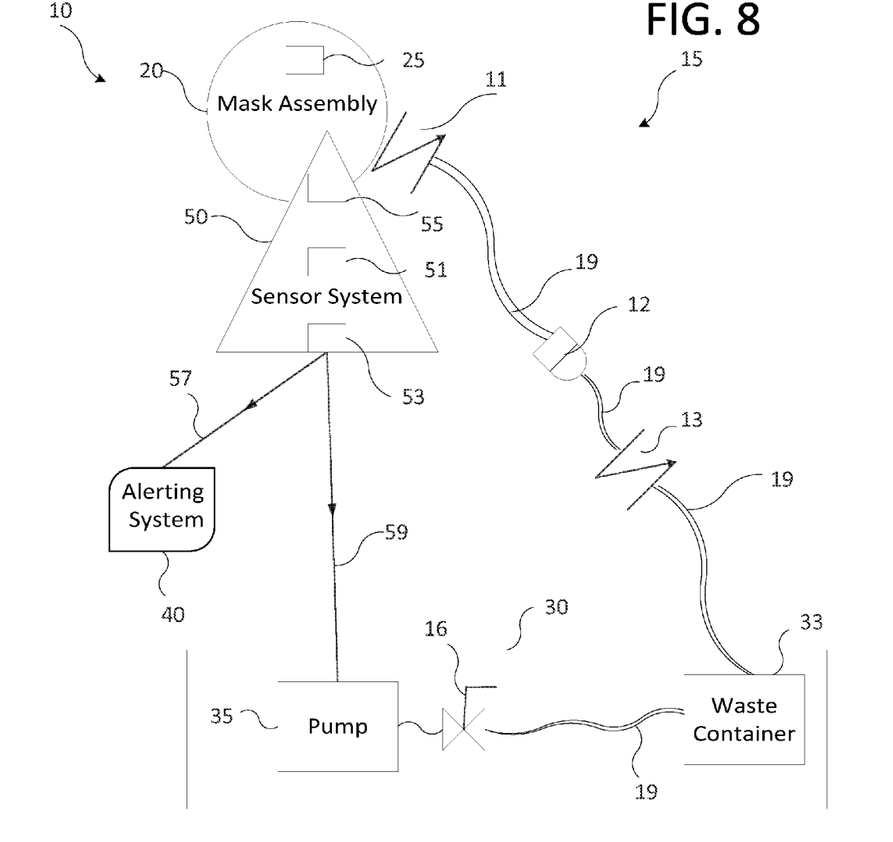
FIG. 8 is a diagram of the tubing assembly of the first and second embodiments of the anti-aspiration medical mask system of the present invention.

In the first aspect of the first embodiment (as seen in overview in FIG. 1) and in the first aspect of the second embodiment (as seen in overview in FIG. 6), the anti-aspiration mask system 10 includes the mask assembly 20, a suction system 30, an alerting system 40, an aspiration-detecting sensor system 50 and a tubing assembly 15 (FIG. 8). In the second aspects of the first embodiment (as seen in FIG. 2) and of the second embodiment (as seen in FIG. 7), the mask system 10 additionally includes a control system 60.

In both embodiments the mask assembly 20 comprises a mask body 25 for covering the wearer's mouth that is integrated with the aspiration-detecting sensor system 50. The aspiration-detecting sensor system 50 both detects aspiration and/or effluent and supplies an aspiration-detected signal, which is supplied, wirelessly or by a wired connection, to both one or more alerting devices 41, 43, 45 and a suction assembly 30. Upon receipt of the aspiration-detected signal, the suction assembly 30 provides suction to tubing 19 attached to the mask body 25 to suction any foreign material from the mask body 25 and mouth while the alerting device 41, 43, 45 provides an alert that notifies medical personnel of the emergency situation.

Figure 3:
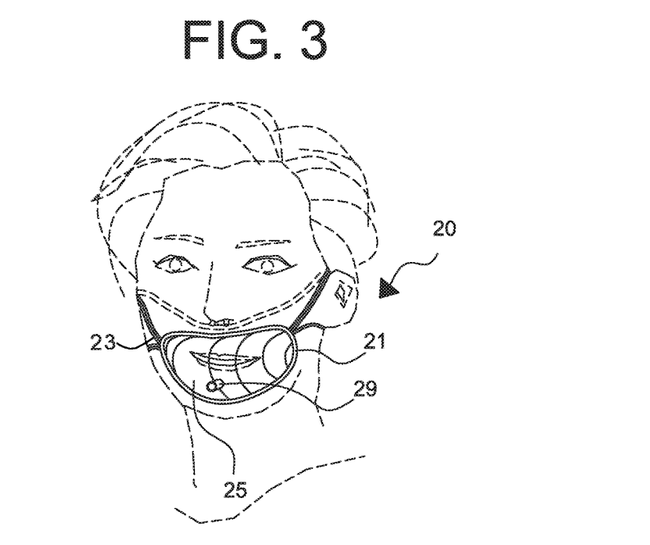
FIG. 3 is a front view schematic of the first and second embodiments of the anti-aspiration medical mask system of the present invention.
Figure 4:
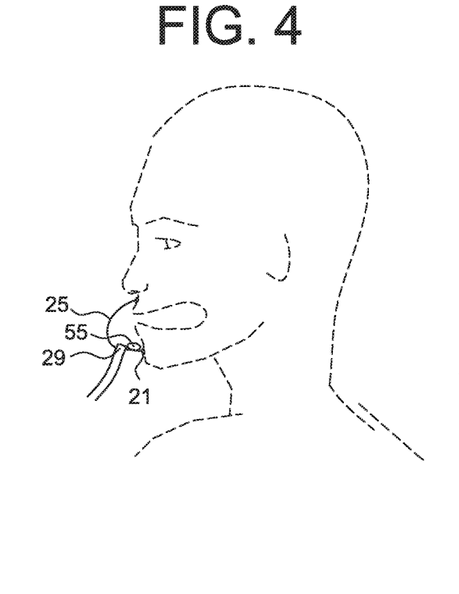
FIG. 4 is a side view schematic of the first embodiment of the anti-aspiration medical mask system of the present invention.

As seen in FIG. 3, the mask assembly 20 of both the first and second embodiment includes a mask body 25, a retaining element 23, a perimeter cushion 21, and a vacuum port 29 for connection with a portion of the tubing assembly 15 (FIG. 8). Preferably the mask assembly 20 is disposable. The mask body 25 includes a protruding portion that is spaced away from the wearer's face to form an interior cavity. The mask body 25 covers the mouth area of the wearer 70, who may be receiving oxygen through a nasal cannula 75, as shown, or the mask body 25 may additionally have an inlet means for directing breathing gases into the interior cavity. The retaining element 23 is attached to the mask assembly 20 and configured to hold the mask assembly 20 onto the face of the wearer.

The perimeter cushion 21 provides contact with the area above the mouth, with the area to both sides of the mouth, and with the area below the mouth towards the chin. The perimeter cushion 21 is configured to generally prevent the ingress of ambient gases into the interior cavity (in combination with the retaining element 23 that assists in maintaining the perimeter cushion firmly in place). The perimeter cushion 21 may be formed of a conventional cushioning material, as is known or may become known in the art. For example, an elastomeric material such as silicone, rubber or rubberized silicon may be used or an open or closed foam material may be used.

The mask body 25 is permanently connected to the cushion 21 and the protruding portion of the mask body 25 extends from the cushion 21 outward from the face of the wearer to accommodate the lips of the wearer. The protruding portion extends sufficiently from the face of the wearer to provide comfort without restricting the movement of the lips. The protruding portion may be formed of conventional mask material, as is known or may become known in the art, such as, for example, medical-grade plastic, silicone, rubber, or the like.

The retaining element 23 may be adjustable or non-adjustable and may be, for example, a single strap or double strap, as illustrated in FIG. 3. The retaining element 23 may loop around the ears, may fit over and around the head, or otherwise assist in removably securing the mask body 25 to the face of the wearer. The retaining element 23 may be formed of a conventional material, as is known or may become known in the art. For example, an elastic material or an elastomeric material (such as polycarbonate, polypropylene, silicone, or the like) may be used.

The sensor system 50 (FIGS. 1, 2, 3, 4, 5, 6, 7) of both embodiments includes an aspiration-detecting sensor 55, at least one signal generator 51 to produce an aspiration-detected signal and at least one aspiration signal transmitter 53 to convey the aspiration-detected signal to the suction system 30 and to the alerting system 40. At least a portion of the aspiration-detecting sensor 55 may be located within the interior cavity of the mask body 25. One or multiple types of aspiration-detecting sensors (with the one or more types of sensors referred to generally as element 55) may be incorporated into the mask system.

In the first embodiment, which is designed for a generally alert patient 70 with pharyngeal muscle control, the aspiration-detecting sensor 55 is preferably one or more of the following types of sensor 55: pH sensor, acoustic sensor, pressure sensor, oxygen flow sensor, or the like.

The pH sensor is configured to detect pH levels. A pre-determined pH level is set, below which an aspiration-detected signal will be generated by the aspiration signal generator 51, which may be integrated into the pH sensor or may be separate. Because gastric contents are acidic, the pH levels in the mouth of the patient 70 will typically be lower than normal following any emesis event. The pH sensor 55 is configured to detect this acidity. An advantage to this type of sensor 55 is that numerous sensors of this type are readily available in the marketplace that can be easily set at pre-determined pH levels, though misdirection of oropharyngeal secretions may not be as readily detected as emesis effluent.

An acoustic sensor 55 can be configured to detect the sounds of any emesis event that occurs. The acoustic sensor 55 may also include a microprocessor for determining a baseline for normal sounds, or in the second aspects of the first and second embodiment, the control system 60 may be used to determine a normal range for the particular patient. By using an algorithm to define normal sounds for the particular patient 70, the acoustic sensor 55 may become more accurate over time.

A pressure sensor 55 can detect aspiration by detecting the change in pressure within the mask body 25 due to obstruction in the larynx. An advantage of the pressure sensor 55 is that aspiration due either to the misdirection of oropharyngeal secretions and due to vomiting of gastric contents may be detected. However, the pressure can also change within the mask body 25 due to normal conditions, such as abnormal breathing patterns or the patient's movement, which may make detection by a pressure sensor 55 alone more difficult. Again, an algorithm may be beneficially used by the control system 60 of the second aspects of the first and second embodiments to determine the parameters of a normal range for a particular patient. The pressure sensor system includes the pressure sensor 55 and may include an aspiration signal generator that generates an aspiration-detected signal and/or may include a wired or wireless system allowing the determined pressure to be transmitted to the control system 60.

Obstruction in the larynx will potentially change the pattern of the flow of oxygen, thus allowing an oxygen flow sensor 55 to be used to detect aspirations of either gastric contents or oropharyngeal secretions. A microprocessor with an algorithm for defining a normal baseline for a particular patient 70 can be added to both the pressure sensor and the oxygen flow sensor to reduce false alerts. Optionally, the control system 60, if present, may receive the sensor 55 input, which is input into a determination algorithm for defining the particular patient's normal baseline and range.

Preferably a combination of sensors 55 may be used to increase the accuracy of the mask system 10.

Upon detection of an aspiration or emesis event by one or more of the above sensors 55, an aspiration-detected signal is generated by the signal generator 51 and transmitted via the aspiration signal transmitter 53 to both the suction system 30 and the alerting system 40 either by a wired connection or a wireless transmission. If wireless transmission is used, a wireless transmitter is included in the sensor system 50 and a wireless receiver is included in the alerting system 40 and/or in the suction system 30. For wireless transmission, a conventional transmission protocol, such as Bluetooth, one of the 802.11 Wi-Fi protocols, or other radio wave protocol is preferred, but other wireless technologies such as microwave or infrared systems are within the scope of the invention. If multiple sensors 55 are used, they may all use the same type of connection (wired or wireless) and/or protocol, or they may use multiple types of connections and/or communication protocols.

The tubing assembly 15 for both the first and second embodiments, as shown in FIG. 8, connects the mask body 25 to the suction system 30. The tubing assembly 15 includes at least one check valve 11 and medical tubing 19; it preferably also includes a second check valve 13, a gate valve 16 and a quick release fitting 12. The first check valve 11 is at or near the mask assembly 20 and prevents backflow into the mask body 25. The optional second check valve 13 is disposed between the quick connector 12 and the waste container 33. The second check valve 13 prevents the migration of waste from the waste container 33 toward the mask body 25. Other optional check valves and/or quick connectors may be utilized within the tubing assembly 15, as desired. For example, a second quick connector and/or a third check valve may be used within the tubing between the pump 35 and the waste container 33. A gate valve 16 is disposed between the pump 35 and the waste container 33 and is operable to prevent any suction, allowing an operator to quickly shut off the device, if necessary.

The suction assembly 30 is connected to the distal end of the tubing assembly 15 (FIG. 8). The suction assembly 30 includes both a suction pump unit 35 and a waste container 33. The suction assembly 30 receives the aspiration-detected signal, and, upon receipt of the signal is actuated to provide suction through the tubing assembly 15 to draw any effluent from the mask body 25. Any substances drawn from the mask body 25 are transported to the waste container 33.

The alerting system 40 may include one or more types of alerting devices 41, 43, 45 to alert medical staff. Any of the alerting devices 41, 43, 45 may provide a visual and/or auditory alert. A signal may be sent to a remote nursing station alarm 41, to an in-room alarm 43, to a mobile application (that provides mobile alert 45) that is available on a hand-held display device such as a mobile phone or tablet, or the like. The in-room alarm 43 may be integrated with conventional in-room electronics, such as a monitoring system at the headboard or bedside of the patient 70, or may be a stand-alone alarm. The aspiration-detected signal may also be received at a remote nursing station via remote alarm 41. The remote alarm 41 may be an independent system or may be integrated into the monitoring systems of the nursing station. The mobile application is a software application that may be available for download onto one or more mobile receiving devices available to the medical personnel. The software application utilizes the audio, tactile (such as by vibration), and visual capabilities of the mobile receiving device to actuate the mobile alert 45. The control signal transmitter 63 sends a signal that is directly or indirectly (such as through a secondary transmitter, router, modem, or the like) wirelessly transmitted to the mobile receiving device. The mobile receiving device may be a cellular phone, tablet, nursing station mobile cart, pager, or the like.

To use the anti-aspiration medical mask system of the first embodiment, the mask body 25 is placed over the patient's mouth area with the perimeter cushion 21 seated comfortably around the mouth area and with the retaining element 23 securing the mask in position. The distal portion of the tubing system 15 is connected to the proximal portion of the tubing system 15 by connecting the distal portion of the quick connector 12 to the proximal portion of the quick connector 12. Power is supplied to the pump 35, which is placed in the ready condition.

If an aspiration event is detected by the sensor system 50, the aspiration-detected signal 57, 59 is sent both to the suction system 30 and to the alerting system 40. The suction pump 35 is activated with suction applied to the tubing system 15 and, hence, to the mask body 25 and possibly to the patient's mouth, if open. Any substances in the mask body 25 will be suctioned through the first check valve 11 (FIG. 8) and into the first section of medical tubing 19. The substances then will be suctioned through the second portion of the tubing 19 and through the quick connector 12 into the distal portions of the tubing 19 and into the waste container 33. The alerting system 40 notifies medical personnel who can then respond. After a one-time use, the mask assembly 20 is preferably discarded and replaced.

Referring now to FIG. 2, in the second aspect of the first embodiment of the anti-aspiration medical mask system, a control system 60 is added, providing additional management of the mask system 10. The control system 60 includes a controller 65, a signal receptor 61, and a signal transmitter 63. The controller 65 is a programmable device that accepts digital data as input, processes the digital data according to instructions stored in its memory, and provides output results; it may be implemented as a microprocessor, a microcontroller, or other form of computing device and may utilize one or more integrated circuits. The signal reception device 61 receives one or more aspiration-detected signals either by wired connection or wirelessly and transmits the signals to the controller 65. The controller 65 sends a pump actuation signal 59 to the pump 35 and sends an actuation signal 57 to the alerting system 40.

Figure 5:
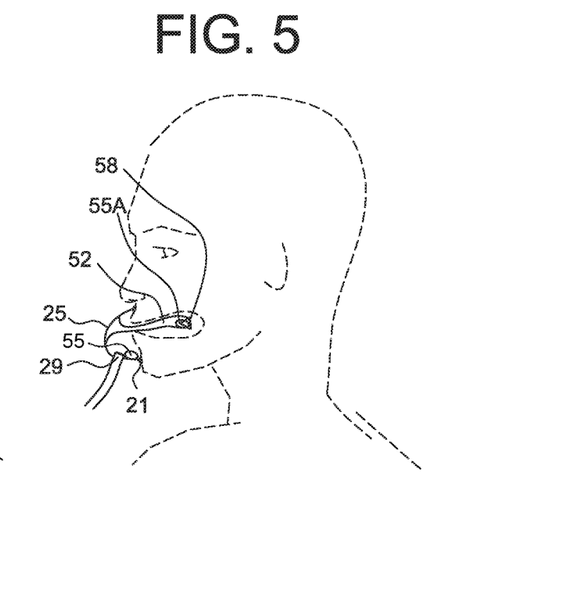
FIG. 5 is a side view schematic of the second embodiment of the anti-aspiration medical mask system of the present invention.
Figure 6:
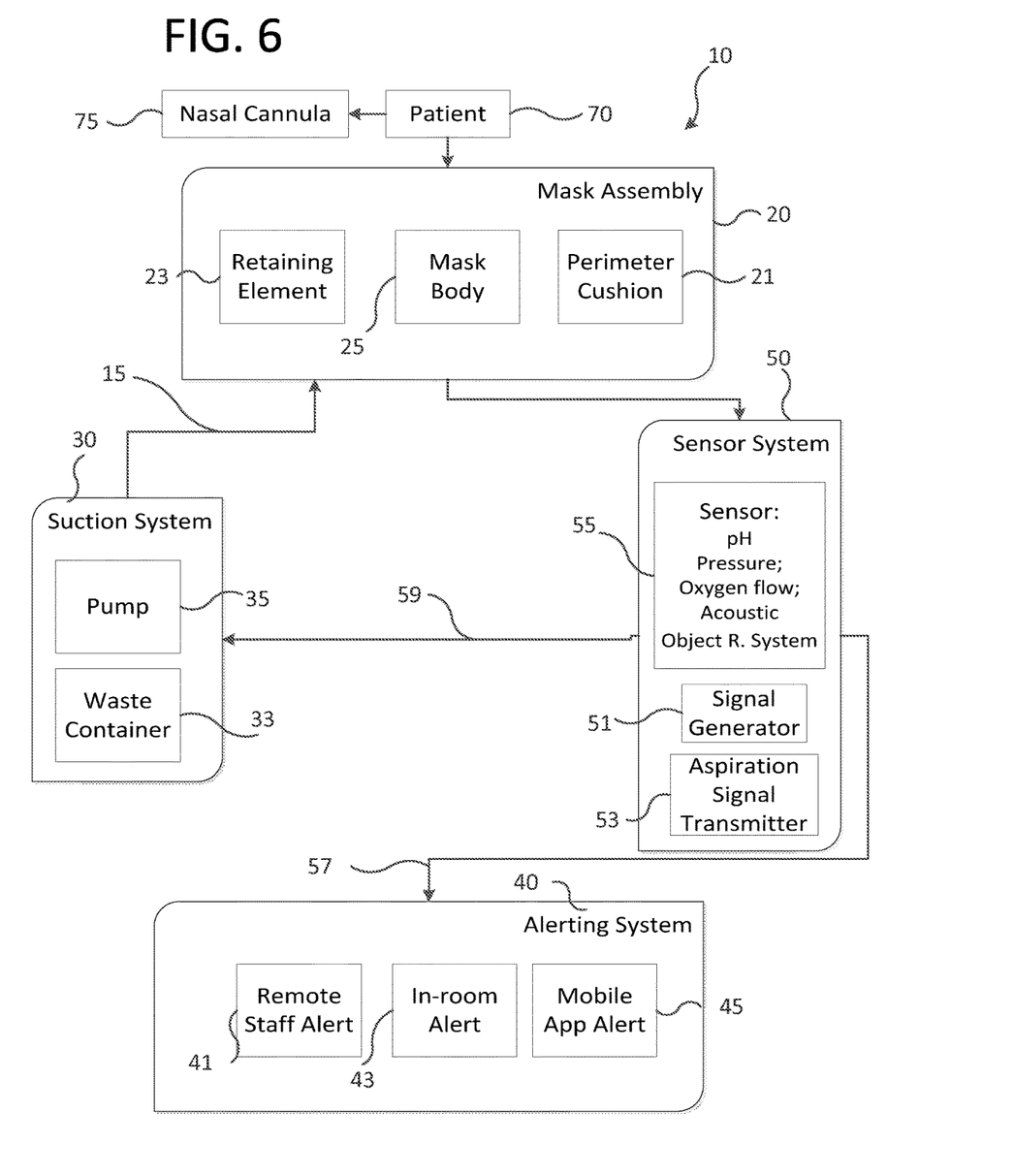
FIG. 6 is a diagram of a first aspect of the second embodiment of the anti-aspiration medical mask system of the present invention.

FIGS. 5-7 illustrate the second embodiment of the anti-aspiration medical mask system 10 of the present invention. The second embodiment addresses the situation in which the patient 70 is unconscious or fully sedated and does not have a cough or gag reflex, so the gastric contents or oropharyngeal secretions may never reach the mask body 25. Thus it is advantageous to detect the substances at the laryngeal inlet. The second embodiment is similar to the first embodiment, with the sensor system 50 including one or more of the above-discussed sensor types, but the sensor system 50 may additionally include an object recognition system, which may be used alone or in combination with the other types of sensors described above.

The object recognition system includes a camera 55A, a light, and object/pattern recognition software. The lighting element is positioned near the camera 55A to provide sufficient light for the images obtained by camera 55A. The camera 55A and lighting element 58 are preferably attached to a projection 52 extending inwardly from the mask body 25 into the interior of the patient's mouth. The inward projection 52 allows the camera 55A and lighting element 58 to be positioned within the posterior of the mouth near the oropharynx. The object/pattern recognition software receives the images from the camera 55A and makes a determination based on a pre-defined algorithm to determine when conditions in the mouth of the patient 70 are abnormal. Optionally, the vacuum port 29 and pressure sensor 55 can be located at the inner end of inward projection 52 with camera 55A. The object/pattern recognition software may be implemented with a stand-alone microprocessor or may be executed by control system 60.

FIG. 6 shows the systems of the first aspect of the second embodiment of the invention, which are integrated without a central control system. FIG. 7 shows the second aspect of the second embodiment, in which the aspiration-detected signal is first routed through the control system 60, as described above.

The control system 60 may also be utilized to receive any or all sensor readings, to establish baseline sensor readings (including removing outliers and developing statistical trends), to make determinations as to whether a received sensor reading is within a normal range, and to control the signals sent to the alerting system 40 and to the suction system 30.

Since many modifications, variations and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A medical mask system, comprising:
a mask assembly comprising a mask body, a retaining element, a vacuum port, and a perimeter cushion; wherein said mask body comprises a protruding portion forming an interior cavity and sized to cover at least the mouth area of a wearer; wherein said perimeter cushion is affixed to said mask body and is configured to provide contact with at least the chin, the upper lip and sides of the mouth of the wearer when the mask system is placed on the wearer's face;
an aspiration-detecting sensor system comprising an aspiration-detecting sensor; wherein at least a portion of said aspiration-detecting sensor is disposed within said interior cavity; and wherein said aspiration-detecting sensor system senses a parameter related to an aspiration event and upon detecting said parameter related to an aspiration event provides a parameter signal; and wherein said parameter signal is utilized in generating an aspiration-detected signal;
a tubing assembly connected to said vacuum port; wherein said tubing assembly comprises a first one-way valve and medical tubing;
a suction system connected to said medical tubing and configured to receive said aspiration-detected signal; said suction assembly comprising a holding container and a suction pump configured to provide suction within said medical tubing upon receipt of said aspiration-detected signal; and
an alerting system comprising at least one alerting device configured to receive said aspiration-detected signal and, upon receipt of said aspiration-detected signal, configured to provide an alert.

2. The medical mask system as recited in claim 1, wherein said aspiration-detecting sensor comprises a pH sensor system comprising a pH sensor; wherein said parameter signal comprises a pH level signal; wherein said pH sensor system detects pH levels and generates said pH signal.

3. The medical mask system as recited in claim 2, wherein said medical mask system further comprises a control system comprising a controller; wherein said controller is configured to receive said pH signal from said pH sensor, make a determination if said pH signal from said pH sensor is outside a pH range, and actuate the sending of said aspiration-detected signal to said alerting system and to said suction system.

4. The medical mask system as recited in claim 1, wherein said aspiration-detecting sensor comprises a pressure sensor system comprising a pressure sensor that detects pressure levels; and wherein said parameter signal comprises a pressure signal.

5. The medical mask system as recited in claim 4, wherein said medical mask system further comprises a control system comprising a controller; wherein said controller is configured to receive said pressure signal from said pressure sensor, make a determination if said pressure signal is outside a pressure range, and actuate the sending of said aspiration-detected signal to said alerting system and to said suction system.

6. The medical mask system as recited in claim 1, wherein said aspiration-detecting sensor comprises an acoustic sensor system comprising an acoustic sensor that detects sounds; and wherein said parameter signal comprises an acoustic signal.

7. The medical mask system as recited in claim 6, wherein said medical mask system further comprises a control system comprising a controller; wherein said controller is configured to receive multiple ones of said acoustic signals, use said multiple ones of said acoustic signals to determine a normal acoustic range for the particular wearer, make a determination if a specific one of said multiple ones of said acoustic signals is outside said normal acoustic range, and actuate the sending of said aspiration-detected signal to said alerting system and to said suction system.

8. The medical mask system as recited in claim 1, wherein said aspiration-detecting sensor comprises an oxygen sensor system comprising an oxygen sensor that detects oxygen; and wherein said parameter signal comprises an oxygen signal.

9. The medical mask system as recited in claim 8, wherein said medical mask system further comprises a control system comprising a controller; wherein said controller is configured to receive multiple ones of said oxygen signals from said oxygen sensor, use said multiple ones of said oxygen signals to determine a normal oxygen range for the particular wearer, make a determination if a specific one of said multiple ones of said oxygen signals is outside said normal oxygen range, and actuate the sending of said aspiration-detected signal to said alerting system and to said suction system.

10. The medical mask system as recited in claim 1, wherein said aspiration-detecting sensor system further comprises an object recognition system comprising a camera and a light.

11. The medical mask system as recited in claim 10, wherein said medical mask the wearer's oropharynx system further comprises a control system comprising a controller and controller memory having stored object/pattern recognition computer code; wherein said controller is configured to receive at least one of video output and still photo output from said camera, use said at least one of video output and still photo output as an input into said object/pattern recognition computer code, make a determination if said received said at least one of video output and still photo output is outside of a normal range of received video output, and actuate the sending of said aspiration-detected signal to said alerting system and to said suction system.

12. The medical mask system as recited in claim 11, wherein said object recognition system further comprises a projection having a distal and proximal end, wherein said proximal end is attached to said mask body and said distal end extends inwardly a distance sufficient to allow said camera to be positioned near the wearer's oropharynx.

13. The medical mask system as recited in claim 12, wherein said vacuum port is disposed at said projection distal end.

14. The medical mask system as recited in claim 13, wherein said aspiration-detecting sensor comprises at least one of a pressure sensor system comprising a pressure sensor that detects pressure levels and an oxygen sensor system comprising an oxygen sensor that detects oxygen levels; and wherein at least one of said pressure sensor and said oxygen sensor is disposed at said projection distal end.

15. The medical mask system as recited in claim 1, wherein said tubing assembly further comprises a second one-way valve and a quick release fitting.

16. A medical mask system, comprising:
  a mask assembly comprising a mask body, a retaining element, a vacuum port, and a perimeter cushion; wherein said mask body comprises a protruding portion forming an interior cavity and sized to cover at least the mouth area of a wearer; wherein said perimeter cushion is permanently affixed to said mask body and is configured to provide contact with at least the chin, the upper lip and sides of the mouth of the wearer when the mask system is placed on the wearer's face;
  an aspiration-detecting sensor system comprising a pH sensor to detect pH levels, a pressure sensor to detect pressure, and an oxygen sensor to detect oxygen levels; wherein said aspiration-detecting sensor system is configured to provide an aspiration-detected signal; wherein at least a portion of said aspiration-detecting system is disposed within said interior cavity;
  a tubing assembly connected to said vacuum port; wherein said tubing assembly comprises a first one-way valve and medical tubing;
  a suction system connected to said medical tubing and configured to receive said aspiration-detected signal; said suction assembly comprising a holding container and a suction pump configured to provide suction within said medical tubing upon receipt of said aspiration-detected signal;
  an alerting system comprising at least one alerting device configured to receive said aspiration-detected signal and, upon receipt of said aspiration-detected signal, configured to provide an alert; and
  a control system comprising a controller and controller memory; wherein said controller is configured to receive a pH signal from said pH sensor; receive an oxygen signal from said oxygen sensor; receive a pressure signal from said pressure sensor; make a determination if one or more of said pH signal, said oxygen signal, and said pressure signal is outside a normal range; and actuate the sending of said aspiration-detected signal to said alerting system and to said suction system.

17. The medical mask system as recited in claim 16, wherein:
  said aspiration-detecting sensor system further comprises an object recognition system comprising a camera and a light;

wherein said controller memory has stored object/pattern recognition computer code;

wherein said controller further is configured to receive at least one of video output and still photo output from said camera; use said at least one of video output and still photo output as an input into said object/pattern recognition computer code; make a determination if the received said at least one of video output and still photo output is outside of a normal range of received video output; and actuate the sending of said aspiration-detected signal to said alerting system and to said suction system.

18. The medical mask system as recited in claim 17, wherein:

said object recognition system further comprises a projection having a distal and proximal end;

said proximal end is attached to said mask body;

said distal end extends inwardly a distance sufficient to allow said camera to be positioned near the wearer's oropharynx; and said vacuum port is disposed at said projection distal end.

19. The medical mask system as recited in claim 18, wherein said tubing assembly further comprises a second one-way valve and a quick release fitting.

\* \* \* \* \*